United States Patent [19]

Kablaoui et al.

[11] 4,035,400

[45] July 12, 1977

[54] PREPARATION OF OMEGA-NITROALKANOIC ACIDS

[75] Inventors: Mahmoud S. Kablaoui, Wappingers Falls; Richard F. Love, Fishkill, both of N.Y.

[73] Assignee: Texaco Inc., New York, N.Y.

[21] Appl. No.: 589,325

[22] Filed: June 23, 1975

[51] Int. Cl.² .................................. C08H 17/36
[52] U.S. Cl. ..................... 260/404; 260/514 J; 260/526 S; 260/526 N; 260/586 R
[58] Field of Search .......... 260/404, 586 R, 526 S, 260/514 J

[56] References Cited

U.S. PATENT DOCUMENTS

| 3,178,471 | 4/1965 | Smiley | 260/526 S |
|---|---|---|---|
| 3,895,071 | 7/1975 | Kablaoui et al. | 260/586 R |
| 3,917,660 | 11/1975 | Sasaki et al. | 260/404 |

OTHER PUBLICATIONS

Matlack, A. S. et al., "Cleavage of 2-Nitrocyclohexanone by Base" J. Org. Chem. 32, June 1967 – pp. 1995–1996.
Hackh's Chemical Dictionary – "Base" p. 101.

*Primary Examiner*—Helen M. McCarthy
*Attorney, Agent, or Firm*—Thomas H. Whaley; Carl G. Ries; George J. Darsa

[57] ABSTRACT

A method of preparing an omega-nitroalkanoic acid is provided by contacting an ammonium, Group IA or Group IIA metal salt of a nitrocycloalkanone with an acidic mineral acid salt in an aqueous medium.

15 Claims, No Drawings

PREPARATION OF OMEGA-NITROALKANOIC ACIDS

BACKGROUND OF THE INVENTION

This invention relates to a novel method of preparing omega-nitroalkanoic acids and particularly to the preparation of omega-nitroalkanoic acids from salts of nitrocycloalkanones.

Omega-nitroalkanoic acids can be prepared by multi-step methods involving reaction of an omega chloro or bromo alkanoic acid with sodium nitrate. Many of such halogen acids, however, are not readily available, particularly those having three or more carbon atoms. Converting cyclic lactones to omega-nitroacids is not commercially attractive inasmuch as low yields of product results as well as extensive by-product formation.

We have now found a method whereby omega-nitroalkanoic acids can be produced in exceptionally good yields and in the absence of by-product formation.

It is, therefore, an object of this invention to provide a method for the preparation of omega-nitroakanoic acids in high yield.

Another object of this invention is to provide a method for the preparation of omega-nitroalkanoic acids from salts of cyclic nitroketones in the substantial absence of by-product formation.

Yet another object of this invention is to provide a method for converting a salt of a nitrocycloalkanone to an omega-nitroalkanoic acid.

Other objects and advantages will become apparent from a reading of the following detailed description and examples.

SUMMARY OF THE INVENTION

Broadly, this invention contemplates a method of preparing an omega-nitroalkanoic acid which comprises contacting an ammonium, Group IA or Group IIA metal salt of a cyclic alpha-nitroketone in an aqueous medium. In a preferred embodiment, the contacting is undertaken in the presence of an acidic mineral acid salt.

In accordance with this invention the salt of the cyclic alpha-nitroketone converted to the omega-nitroalkanoic acid corresponds to the formula:

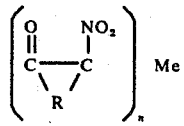

where R is a polymethylene radical of from 1 to 22 carbon atoms or a substituted polymethylene radical of 2 to 22 carbons containing one or more substituents selected from the group consisting of alkyl or aryl and where Me is $NH_4$, a Group IA metal or a Group IIA metal and where $n$ is 1 or 2. Illustrative of the Group IA metals are lithium, sodium and potassium and the Group IIA metals are represented by magnesium, calcium, strontium and barium. The preferred nitroketone salts are those of ammonium, sodium, calcium and magnesium with the ammonium salt being highly preferred.

By the method of this invention the salt of the cyclic nitroketone is converted to an omega-nitroalkanoic acid of the formula:

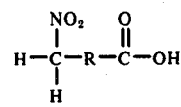

where R is as heretofore defined. When Me is ammonium, ammonia is formed by the method. When Me is a Group IA or IIA metal, the omega-nitroacid is isolated by treating the metal salt of the nitroacid with acetic, formic or a mineral acid. It will be be appreciated that the nitro acid is formed by a method whereby the salt of the nitroketone is transformed to the omege-nitroalkanoic acid through conversion and cleavage. Illustrative of the nitro acids prepared by the instant method we mention omega-nitropropanoic acid, omega-nitrobutanoic acid, omega-nitropentanoic acid, omega-nitro-3-methylpentanoic acid, omega-nitrohexanoic acid, omega-nitroheptanoic acid, omega-nitrodecanoic acid, omega-nitrododecanoic acid, omega-nitrotetradecanoic acid, omega-nitroeicosanoic acid.

By this invention, the nitro acids are prepared from salts of cyclic alpha-nitroketones corresponding to the formula above and include as starting materials, for example, the following ammonium salts: ammonium 2-nitrocyclopropanone, ammonium 2-nitrocyclobutanone, ammonium 2-nitrocyclopentanone, ammonium 2-nitro-3-methylcyclopentanone, ammonium 2-nitrocyclohexanone, ammonium 2-nitrocycloheptanone, ammonium 2-nitrocyclooctanone, ammonium 2-nitrocyclodecanone, ammonium 2-nitrocyclododecanone, ammonium 2-nitrocyclopentadecanone, ammonium 2-nitrocyclohexadecanone, ammonium 2-nitrocycloheptadecanone, and ammonium 2-nitrocycloeicosanone. Mixtures of ammonium salts of cyclic nitroketones can also be employed and provide as product mixtures of the nitro acids. The corresponding Group IA and IIA metal salts are also contemplated and illustrations of the same are sodium 2-nitrocyclopropanone, potassium 2-nitrocyclobutanone, lithium 2-nitrocyclopentanone, magnesium 2-nitrocyclohexanone, calcium 2-nitrocyclooctanone, barium 2-nitrocyclodecanone, strontium 2-nitrocyclododecanone as well as mixtures of Group IA or Group IIA salts of nitroketones. The half salts of the Group IIA metals are also contemplated by this method.

The salts of the cyclic nitroketones employed as starting materials and illustrated above can be prepared from cyclic alkenes corresponding to the formula:

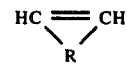

where R is as heretofore defined by simultaneously contacting the cyclic alkene or mixtures of cyclic alkenes with dinitrogen tetroxide and oxygen in a first stage at a temperature between about −40° and 20° C. employing a mole ratio of alkene to dinitrogen tetroxide to oxygen of between about 1:1:1 and 1:1.5:30 to form an intermediate peroxy compound and thereafter contacting the intermediate peroxy compound in a second stage with a denitrating agent of the type known to the art such as dimethylformamide, diethylformamide, dimethylacetamide, dimethylsulfoxide, diethylsulfoxide, tetramethylurea, tetraethylurea, hexamethylenephosphoramide, 1-methyl-2-pyrrolidinone, 1-ethyl-2-pyrrolidinone, 1-isobutyl-2-pyrrolidinone and 1,3-dimethyl-2-pyrrolidinone. The contacting with a denitrating agent is undertaken under conditions of agitation and at a temperature of between about −60° and 70° C., preferably 0° to 40° C. using a mole ratio of denitrating agent to peroxy compound of about 1:1 to about 20:1 to form the cyclic nitroalkanone. Alternatively, stages one and two can be undertaken simultaneously to form the cyclic nitroalkanone. To promote the contact of the reactants in the individual or combined stages, an inert liquid diluent having a boiling point between about 30° and 100° C. is employed such as n-hexane, n-heptane, carbon tetrachloride and benzene. The cyclic nitroketone product can, if desired, be recovered by standard recovery procedures, for example by filtration of the solids after the addition of the reaction mixture to water or by distillation. The nitroketone is converted to the designated salt by contacting the cyclic nitroketone with about 1 to 10, preferably about 1 to 1.1, moles of ammonia, a Group IA metal hydroxide or a Group IIA metal oxide or hydroxide per mole of nitroketone at a temperature of about −10° to 30° C.

In another embodiment, the reaction mixture above containing the cyclic nitroketone is contacted with about 2 to 10, preferably about 2 to 2.1, moles of ammonia, Group IA metal hydroxide or Group IIA metal hydroxide or oxide, thereby converting the cyclic nitroketone to the corresponding ammonium, Group IA or Group IIA metal salt. The salts, so formed, are insoluble in the product formed from the aforementioned nitrooxidation and denitration reactions and are easily separated therefrom employing any well-known technique as for example filtration, centrifugation or decantation.

In one embodiment, the method of this invention comprises heating the salt of the cyclic nitroketone as heretofore described at a temperature of about 50° to 100° C., preferably about 90° to 100° C., with an acidic mineral acid salt in an aqueous medium to form the omega-nitroalkanoic acid. Generally, from 10 to 100 parts by weight or water per part of nitroketone salt can be employed. In a preferred embodiment, the method is undertaken in the presence of an acid mineral acid salt. In the course of transforming the nitroketone salt to the desired nitroacid, the reaction may be accompanied by foaming. The presence of an acidic mineral acid salt is beneficial in enabling the reaction to be conducted in the absence of foam. Acidic mineral acid salts contemplated herein include ammonium chloride, ammonium nitrate, ammonium sulfate, ammonium hydrogen sulfate, ammonium phosphate, or calcium nitrate. In highly preferred embodiments, we employ ammonium nitrate or calcium nitrate. The mole ratio of cyclic nitroketone salt to acidic mineral acid salt employed herein can range from about 1:0.01 to 1:2 and preferably from about 1:0.5 to 1:1.5. At the completion of the reaction, the omega-nitroalkanoic acid can be recovered by, for example, simple filtration when ammonia is used, as for example when the ammonium salt of the cyclic nitroketone is used in conjunction with ammonium nitrate, and the nitroacid is obtained directly from the reaction mixture. Further, when the ammonium salt of the nitrocycloalkanone is employed as the starting material, ammonia is separated from the nitroacid product by refluxing employing a nitrogen or air sweep. When a Group IA or IIA metal salt of the cyclic nitroketone is used, the metal component is separated as the metal salt of the nitroacid and the nitroacid is recovered by acidification of the salt with a mineral acid, formic acid or acetic acid.

By the instant method, salts of cyclic nitroketones can be selectively converted to omega-nitroalkanoic acids in very high yields. The nitroacids prepared according to this invention are useful as chemical intermediates for the preparation of polymers and synthetic fibers.

In order to more fully illustrate the nature of this invention and the manner of practicing the same, the following examples are presented.

EXAMPLE I

Benzene (200 milliliters), cyclododecene (33.2 grams, 0.20 mole) and dimethylformamide (20 milliliters, 0.258 mole) were charged to a 500 milliliter flask equipped with a condenser. To the stirred mixture cooled to 10° C., there was introduced a mixture of dinitrogen tetroxide (18.5 grams, 0.201 mole) and oxygen at a 1:5 volume to volume ratio over a period of four hours. The oxygen stream was continued for an additional thirty minutes followed by a nitrogen purge.

The reaction mixture, maintained at 10°–15° C. was treated with gaseous ammonia (3.5 grams, 0.205 mole) over a period of thirty minutes. The solids formed (67 grams), consisting of a mixture of ammonium nitrate and the ammonium salt of 2-nitrocyclododecanone were collected by filtration and transferred to a flask containing 300 milliliters of water. After refluxing for three hours and sweeping with nitrogen, the mixture was cooled and filtered. The solid (44 grams, 90 percent yield) was identified as 12-nitrododecanoic acid basis analysis by infrared and nuclear magnetic resonance.

EXAMPLE II

Into a flask equipped with a gas inlet thermometer and condenser, there was charged 11.0 grams (0.1 mole) of cyclooctene and 100 milliliters of carbon tetrachloride. To this solution, maintained at a temperature of 10° C., there was introduced oxygen at the rate of 100 milliliters per minute and 9.2 grams (0.1 mole) of dinitrogen tetroxide at the rate of 0.05 gram per minute over a period of three hours. At the end of the dinitrogen tetroxide-oxygen addition period, 11 grams (0.15 mole) of dimethylformamide denitrating agent were added over a period of one-quarter hour while maintaining the temperature at 10° C.

To the above reaction mixture, maintained at 10° C., there was introduced 5.6 grams (0.1 mole) of calcium oxide. The solids composed of calcium nitrate and the calcium salt of 2-nitrocyclooctanone were separated from the crude composition by filtration and weighed 27.0 grams.

The solids were charged into a 500 milliliter flask and 200 milliliters of water were added and the reaction mixture was heated at 100° C. for three hours. The mixture was cooled, acidified with 6N hydrochloric acid and filtered to give 17.0 grams (90 percent yield) of 8-nitrooctanoic acid identified by infrared and nuclear magnetic resonance.

We claim:

1. A method of preparing an omega-nitroalkanoic acid in the substantial absence of by-product formation which comprises contacting an ammonium salt of a cyclic alpha-nitroketone in an aqueous medium at a temperature of about 50° to 100° C.

2. A method according to claim 1 wherein said contacting is undertaken in the presence of an acidic mineral acid salt which is ammonium chloride, ammonium nitrate, ammonium sulfate, ammonium hydrogen sulfate, ammonium phosphate or calcium nitrate.

3. A method according to claim 1 wherein said contacting is at a temperature of about 90° to 100° C.

4. A method according to claim 1 wherein said salt of the nitroketone corresponds to the formula:

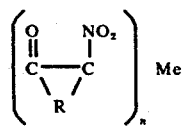

where R is a polymethylene radical of from 1 to 22 carbons or an alkyl or aryl substituted polymethylene radical of 2 to 22 carbon atoms where Me is $NH_4$ and where $n$ is 1.

5. A method according to claim 1 wherein said nitroketone salt is ammonium 2-nitrocyclopropanone.

6. A method according to claim 1 wherein said nitroketone salt is ammonium 2-nitrocyclododecanone.

7. A method according to claim 1 wherein said nitroketone salt is ammonium 2-nitrocyclopentanone.

8. A method according to claim 1 wherein said nitroketone salt is ammonium 2-nitrocyclohexanone.

9. A method according to claim 2 wherein said acidic salt is ammonium nitrate.

10. A method of preparing an omega-nitroalkanoic acid in the substantial absence of by-product formation which comprises (a) contacting a Group IIA metal salt of a cyclic alpha-nitroketone in an aqueous medium at a temperature of about 50° to 100° C. and (b) subsequently acidifying the product of (a) with a mineral acid, formic acid or acetic acid thereby forming said omega-nitroalkanoic acid.

11. A method according to claim 10 wherein said contacting is undertaken in the presence of an acidic mineral acid salt which is ammonium chloride, ammonium nitrate, ammonium sulfate, ammonium hydrogen sulfate, ammonium phosphate or calcium nitrate.

12. A method according to claim 10 wherein said contacting is at a temperature of about 90° to 100° C.

13. A method according to claim 10 wherein said salt of the nitroketone corresponds to the formula:

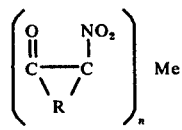

where R is a polymethylene radical of from 1 to 22 carbon atoms or an alkyl or aryl substituted polymethylene radical of 2 to 22 carbon atoms where Me is a Group IIA metal and where $n$ is 1 or 2.

14. A method according to claim 10 wherein said nitroketone salt is calcium 2-nitrocyclododecanone.

15. A method according to claim 11 wherein said acid salt is calcium nitrate.

* * * * *